(12) United States Patent (10) Patent No.: US 12,179,220 B2
Calderon et al. (45) Date of Patent: Dec. 31, 2024

(54) APPARATUS, SYSTEMS AND METHODS FOR STORING, TREATING AND/OR PROCESSING BLOOD AND BLOOD COMPONENTS

(71) Applicant: Fenwal, Inc., Lake Zurich, IL (US)

(72) Inventors: Carlos Calderon, Waukegan, IL (US); Christopher Gassman, Crystal Lake, IL (US); David S. Brown, Lake Barrington, IL (US)

(73) Assignee: Fenwal, Inc., Lake Zurich, IL (US)

(*) Notice: Subject to any disclaimer, the term of this patent is extended or adjusted under 35 U.S.C. 154(b) by 0 days.

(21) Appl. No.: 18/624,536

(22) Filed: Apr. 2, 2024

(65) Prior Publication Data

US 2024/0253061 A1 Aug. 1, 2024

Related U.S. Application Data

(63) Continuation of application No. 17/567,202, filed on Jan. 3, 2022, which is a continuation of application (Continued)

(51) Int. Cl.
*A61J 1/10* (2006.01)
*A61M 1/02* (2006.01)
(Continued)

(52) U.S. Cl.
CPC .................. *B04B 5/12* (2013.01); *A61J 1/10* (2013.01); *A61M 1/0209* (2013.01);
(Continued)

(58) Field of Classification Search
CPC .......... B04B 5/12; A61J 1/10; A61M 1/0209; A61M 1/025; A61M 39/12; A61M 39/18; B01D 21/262
See application file for complete search history.

(56) References Cited

U.S. PATENT DOCUMENTS 3,416,528 A 12/1968 Kahn
4,025,618 A 5/1977 Garber et al.
(Continued)

FOREIGN PATENT DOCUMENTS

CN 1018491 B 9/1992
CN 1561243 A 1/2005
(Continued)

OTHER PUBLICATIONS

Partial European Search Report For Application No. 18181692.7 dated Dec. 7, 2018.
(Continued)

*Primary Examiner* — Chester T Barry
(74) *Attorney, Agent, or Firm* — Cook Alex Ltd.

(57) ABSTRACT

Apparatus, systems and methods are disclosed relating to certain aspects of blood processing, collecting or storing, including method and system for automated authentication, processing device with scanner, blood container with two dimensional barcode, blood collection containers, blood container label and related tracking method, integrated container system, and processing device with sterile connection device.

20 Claims, 6 Drawing Sheets

Related U.S. Application Data

No. 16/902,437, filed on Jun. 16, 2020, now Pat. No. 11,247,216, which is a continuation of application No. 15/757,496, filed as application No. PCT/US2016/051438 on Sep. 13, 2016, now Pat. No. 10,730,058.

(60) Provisional application No. 62/218,214, filed on Sep. 14, 2015, provisional application No. 62/218,242, filed on Sep. 14, 2015, provisional application No. 62/218,234, filed on Sep. 14, 2015.

(51) Int. Cl.
| | |
|---|---|
| *A61M 39/12* | (2006.01) |
| *A61M 39/18* | (2006.01) |
| *B01D 21/26* | (2006.01) |
| *B04B 5/12* | (2006.01) |

(52) U.S. Cl.
CPC ............ *A61M 1/025* (2013.01); *A61M 39/12* (2013.01); *A61M 39/18* (2013.01); *B01D 21/262* (2013.01); *A61J 2205/00* (2013.01); *A61J 2205/10* (2013.01); *A61M 2205/3303* (2013.01); *A61M 2205/3393* (2013.01); *A61M 2205/6063* (2013.01); *A61M 2205/6072* (2013.01); *A61M 2230/207* (2013.01)

(56) References Cited

U.S. PATENT DOCUMENTS

| | | | |
|---|---|---|---|
| 4,157,723 A | 6/1979 | Granzow et al. | |
| 4,181,140 A | 1/1980 | Bayham et al. | |
| 4,270,534 A | 6/1981 | Adams | |
| 4,326,518 A * | 4/1982 | Williams ............ | A61M 39/288 |
| | | | 604/533 |
| 4,369,779 A | 1/1983 | Spencer | |
| 4,379,452 A * | 4/1983 | DeVries ............. | A61M 1/3693 |
| | | | 604/6.11 |
| 4,386,622 A | 6/1983 | Munsch | |
| 4,405,079 A * | 9/1983 | Schoendorfer ....... | B04B 5/0428 |
| | | | 494/44 |
| 4,753,697 A | 6/1988 | Shaposka et al. | |
| 4,753,729 A | 6/1988 | Schoendorfer et al. | |
| 4,776,964 A | 10/1988 | Schoendorfer et al. | |
| 4,943,283 A | 7/1990 | Hogan | |
| 5,045,185 A | 9/1991 | Ohnaka et al. | |
| 5,135,667 A | 8/1992 | Schoendorfer | |
| 5,156,701 A | 10/1992 | Spencer et al. | |
| 5,158,630 A | 10/1992 | Shaposka et al. | |
| 5,194,145 A | 3/1993 | Shoendorfer | |
| 5,268,564 A | 12/1993 | Metlitsky | |
| 5,306,269 A | 4/1994 | Lewis et al. | |
| 5,319,184 A | 6/1994 | Gilpin et al. | |
| 5,966,945 A | 10/1999 | Mengel et al. | |
| 6,225,641 B1 | 5/2001 | Stoner et al. | |
| 7,037,428 B1 * | 5/2006 | Robinson ............ | A61M 1/3693 |
| | | | 604/6.02 |
| 9,033,948 B2 | 5/2015 | Payrat et al. | |
| 9,038,823 B2 | 5/2015 | Calderon et al. | |
| 9,247,902 B2 | 2/2016 | Kashmirian et al. | |
| 9,533,135 B2 | 1/2017 | Kusters et al. | |
| 10,730,058 B2 * | 8/2020 | Calderon ............... | A61J 1/10 |
| 11,247,216 B2 * | 2/2022 | Calderon ............... | A61J 1/10 |
| 2003/0007423 A1 | 4/2003 | Hickle et al. | |
| 2003/0106969 A1 | 6/2003 | Dillon et al. | |
| 2003/0195452 A1 | 10/2003 | Hunley et al. | |
| 2004/0230153 A1 | 11/2004 | Demay et al. | |
| 2006/0196951 A1 | 9/2006 | Lowmaster | |
| 2007/0272738 A1 * | 11/2007 | Berkun ................ | G09B 21/00 |
| | | | 235/375 |
| 2010/0133203 A1 | 6/2010 | Walker et al. | |
| 2010/0291619 A1 | 11/2010 | Robinson et al. | |
| 2011/0192745 A1 | 8/2011 | Min | |
| 2011/0281346 A1 | 11/2011 | Halpern et al. | |
| 2012/0015794 A1 | 1/2012 | Holmes | |
| 2012/0251411 A1 | 10/2012 | Jeon | |
| 2012/0265099 A1 | 10/2012 | Goodnow, II et al. | |
| 2012/0269679 A1 | 10/2012 | Payrat et al. | |
| 2013/0153048 A1 | 6/2013 | Schwalm et al. | |
| 2014/0077488 A1 | 3/2014 | Wegener et al. | |
| 2015/0060549 A1 | 3/2015 | Hirono et al. | |
| 2015/0073832 A1 | 3/2015 | Goodnow, II et al. | |
| 2015/0128096 A1 * | 5/2015 | Rizvi ................... | G06F 3/1454 |
| | | | 715/863 |
| 2015/0343123 A1 | 12/2015 | Bancroft et al. | |
| 2015/0367120 A1 * | 12/2015 | Kusters ................ | A61M 39/18 |
| | | | 137/15.09 |
| 2015/0367569 A1 | 12/2015 | Kusters et al. | |
| 2016/0113721 A1 | 4/2016 | Seremjian et al. | |
| 2016/0289638 A1 | 10/2016 | Lynn et al. | |
| 2017/0160293 A1 * | 6/2017 | Paglia ................. | A61K 35/18 |

FOREIGN PATENT DOCUMENTS

| | | |
|---|---|---|
| CN | 101342955 A | 1/2009 |
| CN | 102947009 A | 2/2013 |
| CN | 103002932 A | 3/2013 |
| CN | 103415329 A | 11/2013 |
| CN | 103501853 A | 1/2014 |
| CN | 104582669 A | 4/2015 |
| EP | 1153742 A1 | 11/2001 |
| JP | 2002119587 A | 4/2002 |
| WO | WO 02/070035 A2 | 9/2002 |
| WO | WO 03/026558 A2 | 4/2003 |
| WO | WO 03/063930 A1 | 8/2003 |
| WO | WO 2012/125472 A1 | 9/2012 |
| WO | WO 2012/154572 A1 | 11/2012 |
| WO | WO 2014/039086 A1 | 3/2014 |
| WO | WO 2014/092004 A1 | 6/2014 |
| WO | WO 2015/184462 A1 | 12/2015 |

OTHER PUBLICATIONS

PCT Notification Concerning Transmittal Of International Preliminary Report On Patentability For Application No. PCT/US2016/051438 dated Mar. 29, 2018.

* cited by examiner

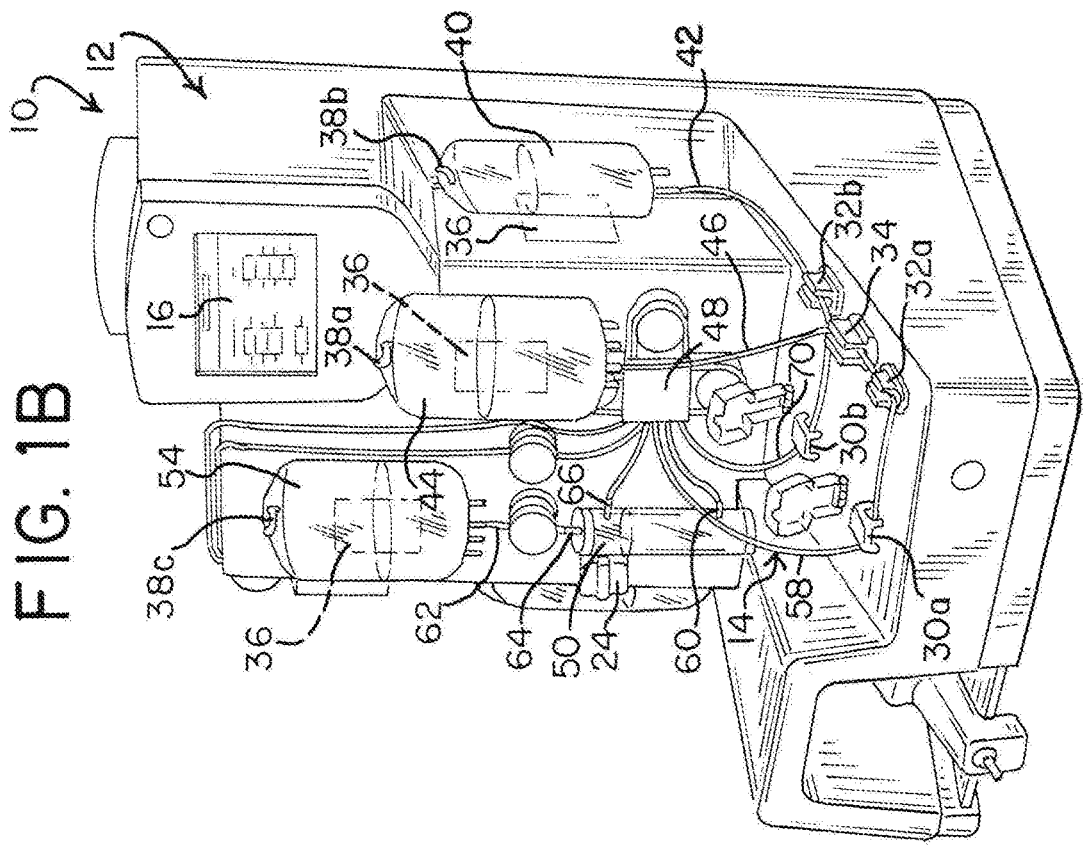
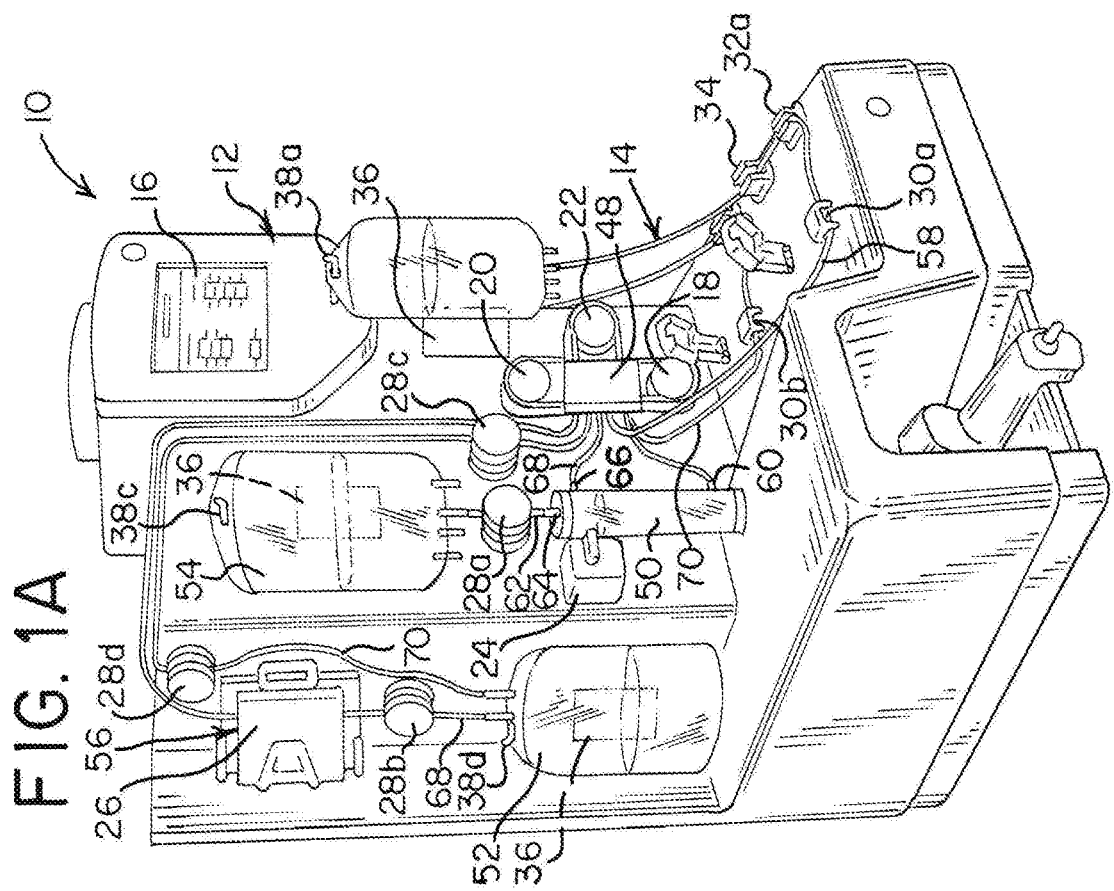

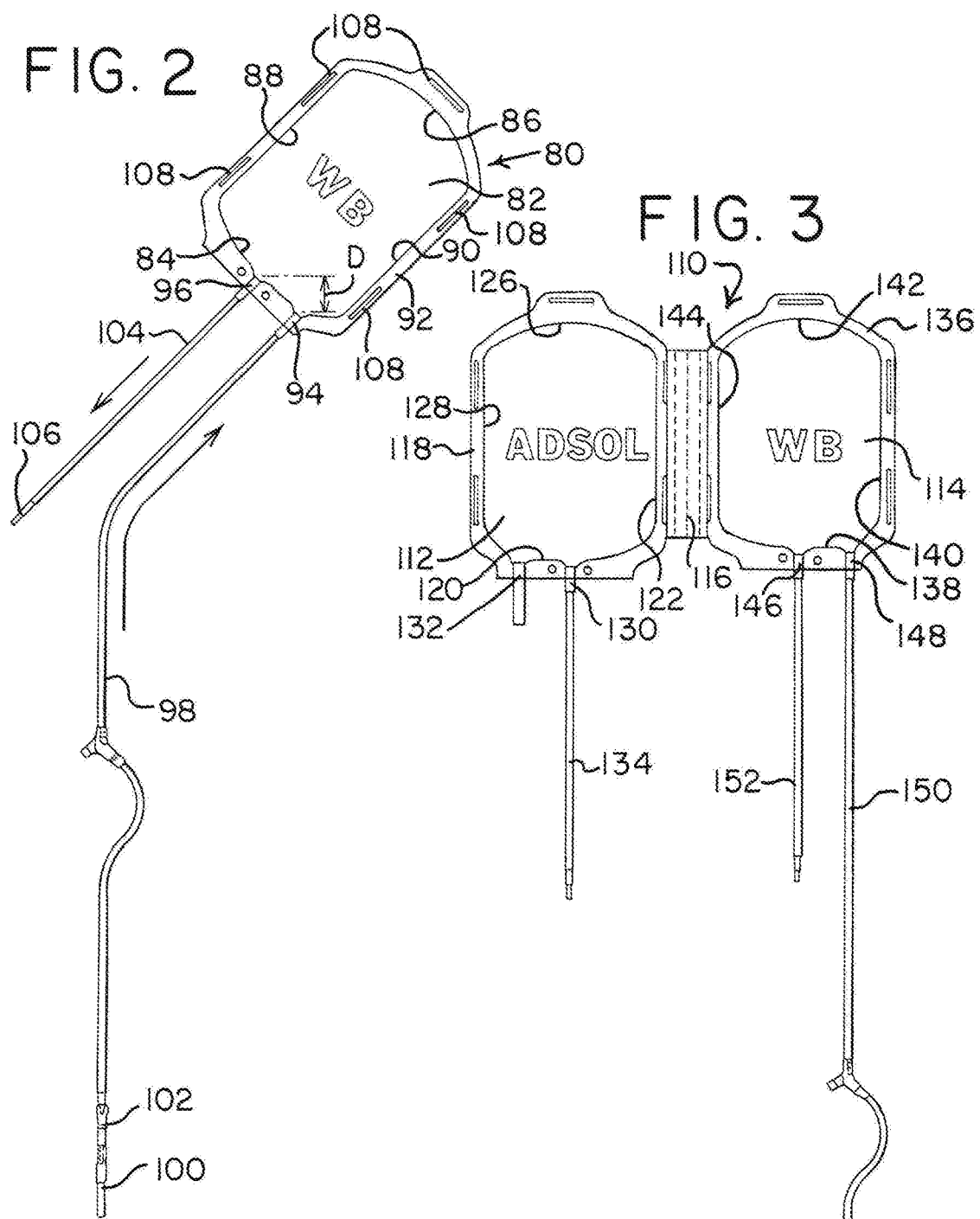

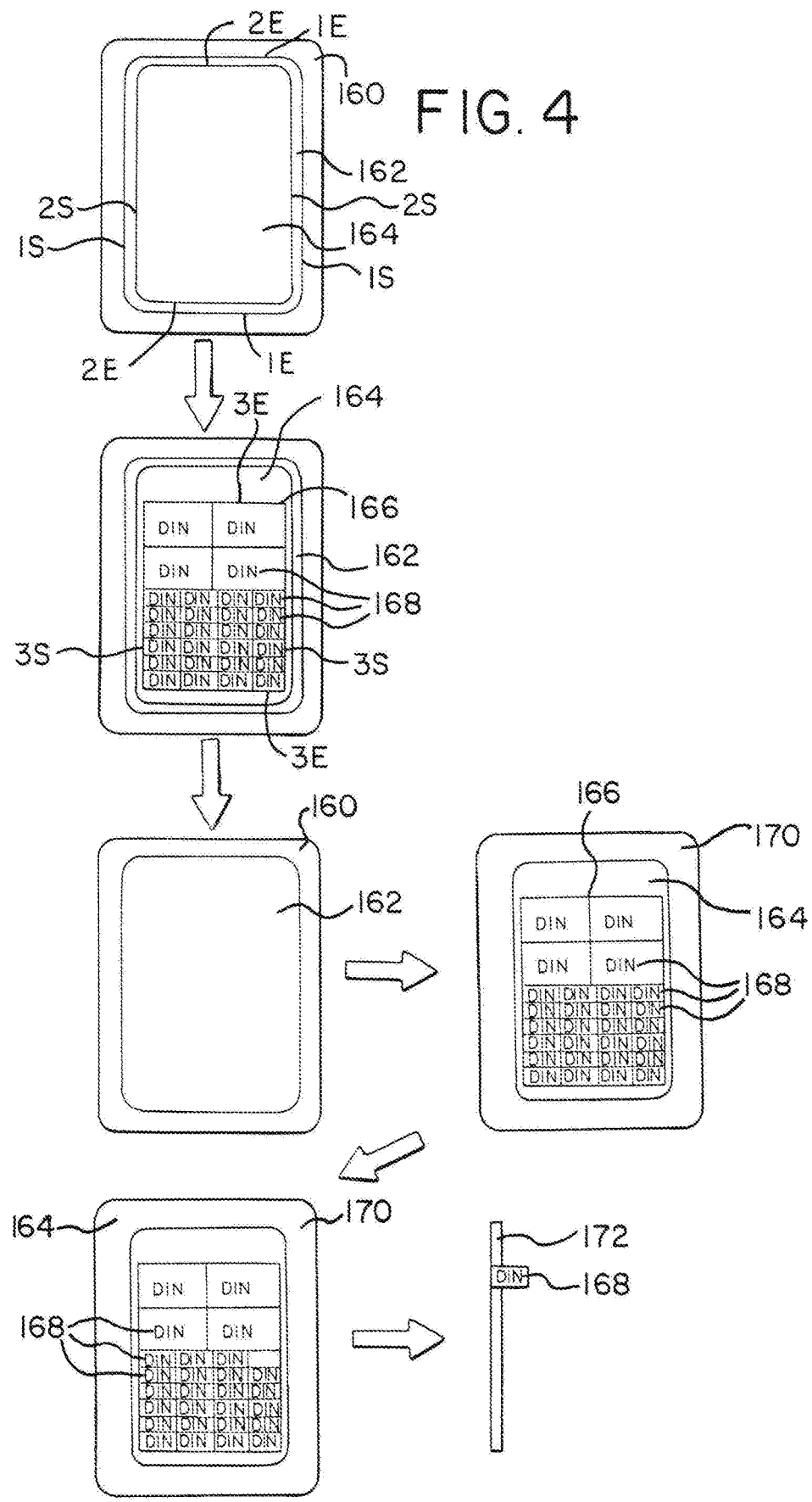

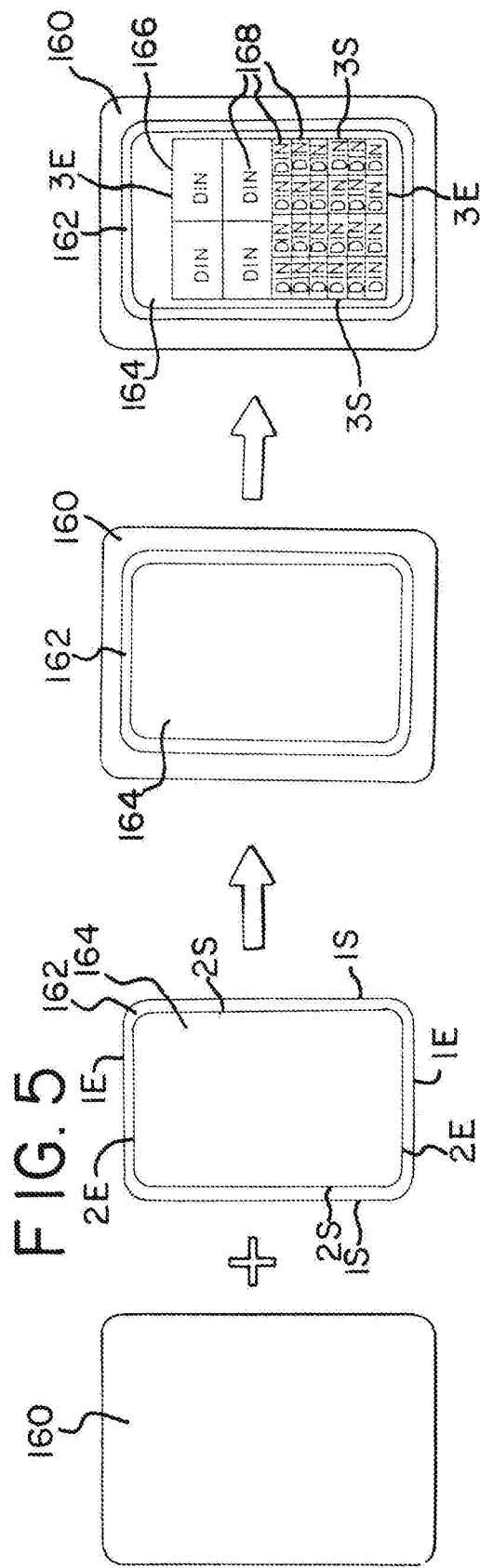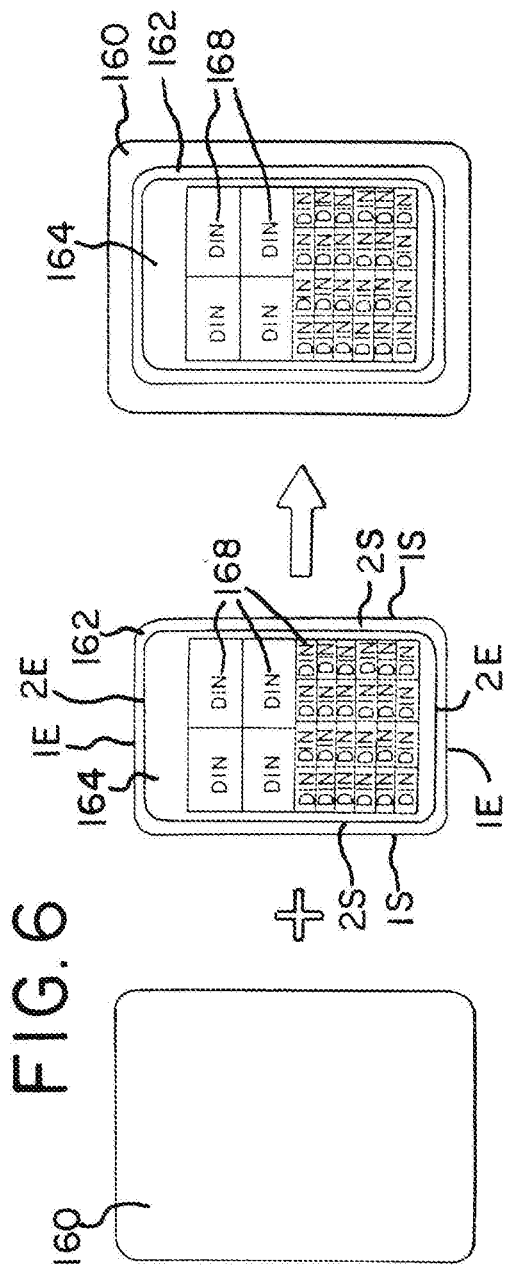

ered to as membrane separators. In such membrane separators. In such membrane
APPARATUS, SYSTEMS AND METHODS FOR STORING, TREATING AND/OR PROCESSING BLOOD AND BLOOD COMPONENTS

CROSS REFERENCE TO RELATED APPLICATIONS

This application is a continuation of U.S. patent application Ser. No. 17/567,202, filed Jan. 3, 2022, which is a continuation of U.S. patent application Ser. No. 16/902,437, filed Jun. 16, 2020, which is a continuation of U.S. patent application Ser. No. 15/757,496, filed Mar. 5, 2018, which is a U.S. National Stage of PCT International Patent Application No. PCT/US2016/051438, filed Sep. 13, 2016, which claims priority to and the benefit of U.S. Provisional applications 62/218,214 filed Sep. 14, 2015; 62/218,234 filed Sep. 14, 2015; and 62/218,242 filed Sep. 14, 2015, all of which are hereby incorporated by reference.

This application relates generally to blood and blood component storing, treating and/or processing, and related novel apparatus, systems and methods associated with such storing, treating and/or processing.

It is well known to collect whole blood from donors using manual collection procedures through blood drives, donor visits to blood centers or hospitals and the like. In such procedures, blood is typically collected by simply flowing it from the donor under the force of gravity and venous pressure into a collection container (e.g., a flexible pouch or bag). Although various blood collection instruments may be used to aid or expedite the collection of blood or blood components.

The collection container in manual collection is often part of a larger pre-assembled arrangement of tubing and containers, sometimes called satellite containers that are used in further processing of the whole blood collected. More specifically, the whole blood is typically first collected in what is called a primary collection container that also contains an anticoagulant, such as but not limited to a solution of sodium citrate, phosphate and dextrose (CPD).

After initial collection, it is a common practice to transport the collected whole blood to another facility or location, sometimes called a "back lab," for further processing. This processing usually entails manually loading the primary collection container and associated tubing and satellite containers into a centrifuge to separate the whole blood into concentrated red cells and platelet-rich or platelet-poor plasma. The separated components may then be expressed from the primary collection container into one or more of the satellite containers and the red cells combined with an additive or preservative solution pre-filled in one of the satellite containers. One such additive solution includes sodium chloride, mannitol, adenine and dextrose, such as marketed under the tradename ADSOL® by Fenwal, Inc. of Lake Zurich, Illinois, USA, which is an affiliate of Fresenius Kabi AG of Bad Homburg, Germany. After the above steps, the blood components may be again centrifuged, if desired, for example to separate platelets from plasma. As apparent from this description, this process is labor intensive, time consuming and subject to human error.

There have been continuing efforts to automate the apparatus and systems used in the post-collection processing of whole blood, and recently it has been proposed to employ an automated blood component separator for such post-collection processing. While many of the prior blood separation devices and procedures have employed centrifugal separation principles, there is another class of devices that employs relatively rotating surfaces, at least one of which carries a porous membrane.

Such systems may include a membrane-covered spinner, having an interior collection system, disposed within a stationary shell or housing. Alternatively, an inner surface of the stationary housing may be covered by a membrane, or both the spinner and the housing may include associated membranes. For purposes of this description, these will be referred to as membrane separators. In such membrane separators, blood is fed into an annular space or gap between the spinner and the shell and moves along the longitudinal axis of the shell toward an exit region. Plasma passes through the membrane and exits through an outlet port, while the remaining cellular blood components (red blood cells, platelets, and white cells) remain in the gap and move to exit the region between the spinner and the shell through an exit port. Membrane separators have been found to provide excellent plasma filtration rates, due primarily to the unique flow patterns ("Taylor vortices") induced in the gap between the spinning membrane and the shell. The Taylor vortices help to keep the blood cells from depositing on and fouling or clogging the membrane. Detailed descriptions of membrane separators may be found in U.S. Pat. Nos. 5,194,145; 4,776,964; 4,753,729; and 5,135,667, all of which are incorporated by reference herein.

While membrane separators have been widely used for the collection of plasma, they have not typically been used for the collection of other blood components, specifically red blood cells. One example of a membrane separator used in the collection of separated red blood cells is described in PCT Patent Application Publication No. WO 2014/039086 A1, which is incorporated by reference in its entirety. Further, a system employing such a membrane separator for post-collection processing of whole blood is described in U.S. patent application Ser. No. 14/677,319 filed Apr. 2, 2015, which is also incorporated by reference in its entirety.

The subject matter disclosed herein provides further advances in various aspects of the apparatus, systems and methods that may be employed in whole blood collection and post-collection processing systems, although they are not necessarily limited to such systems. Examples of prior devices or methods may be found in U.S. Pat. No. 9,038,823 and U.S. Published Application US 2012/0269679.

SUMMARY

There are several aspects of the present subject matter which may be embodied separately or together in the devices, systems, and methods described and/or claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto or later amended. For purposes of this description and claims, unless otherwise expressly indicated, "blood" is intended to include whole blood and blood components, such as concentrated red cells, plasma, platelets and white cells, whether with or without anticoagulant or additives. Also the words "imager", "scanner," "imaging", "scanning", "imager/scanner" and scanner/imager", and variations thereof, are used alternatively and interchangeably in this description, with no difference intended unless expressly stated, to refer to devices and/or methods employed by devices that optically view or read an image such as a barcode, logo, label or label portion on a blood container for the non-exclusive purpose of retrieving or capturing information, whether such information be in the form of data encoded into a barcode, an actual image itself, information or data reflected in such an image or that can be derived from such an image, or any combination of these.

The following summary is to acquaint the reader generally with various potential aspects of the present subject matter, and is non-limiting and non-exclusive with respect to the various possible aspects or combinations of aspects. Additional aspects and features may be found in the detailed description herein and/or in the accompanying figures.

Authenticating/Imaging

In one aspect, a method is provided for automated authentication of a blood component container. The method comprises scanning a trade logo carried on a wall of the container; detecting certain characteristic or characteristics of the scanned logo and comparing such characteristic or characteristics against established reference characteristic or characteristics of the trade logo on an authentic blood component container; and determining whether the scanned container is authentic based on comparison of the determined characteristic or characteristics and the established reference characteristic or characteristics. The method is preferably carried out automatically by a programmable controller associated with a blood processing device. In the event of determination of the use of a non-authentic container, an alert may be generated and/or operation of the processing device may be disabled.

In a related aspect, a system may be provided that includes a disposable blood or blood component processing circuit and a durable blood processing device cooperatively associated with the processing circuit for controlling flow through the processing circuit. The processing circuit includes a blood or blood component container with a trade logo carried on an external surface of the container. The processing device includes a scanner configured to scan the logo optically when the container is cooperatively associated with the device and a programmable controller configured to receive signals from the scanner. The controller is programmed to detect certain characteristic or characteristics of the optically scanned logo, compare such characteristic or characteristics against established reference characteristic or characteristics of the trade logo on an authentic blood component container, and determine whether the scanned container is authentic based on comparison of the determined characteristic or characteristics and the established reference characteristic or characteristics. The scanner may also capture an image of the logo and save it or transmit it to a data storage device for future reference and/or as part of process record.

In yet another independent aspect, a processing device is provided for processing medical fluids such as blood or blood components, the processing device including a housing, a container suspension device for suspending a container on the processing device, and a scanning system for scanning at least a portion of a surface of a container that faces the suspension device when suspended thereon. The scanning system comprises a window in the housing adjacent to the location of a container when suspended from the suspension device, and a scanner located within the housing and positioned to scan or image a surface of a suspended container through the window. The scanner is positioned so as to image a selected surface area of the container. The selected surface area may be a label carried on the container and the label may include, without limitation, a barcode, a trade logo such as summarized above, and/or other information or images.

Barcode/Labeling

In one aspect, a blood container is provided that carries a two dimensional barcode on an exterior surface of the container. The barcode may encode at least a manufacturer's part number or catalogue number for the particular blood container. It may also include other information such as an expiration date for the blood container. The blood container is preferably configured to be suspended on a blood processing device and the barcode being located on a side of the container facing the blood processing device when suspended thereon. This allows the barcode to be scanned by a scanner on the device to obtain the encoded information. The encoded information may include all of the manufacture-related information required by the United States Industry Consensus Standard for the Uniform Labeling of Blood and Blood components for blood or a blood component that is to be contained in the container.

In yet a further aspect, a whole blood collection container is provided for collecting whole blood from a donor. The container comprises a wall having an exterior surface, a first panel substantially permanently adhered to the exterior surface of the container wall, a second panel removably adhered to the first panel, the second panel being removable from the first panel for transferring and adhering to a surface of a separate blood component container. The second panel has an exterior surface that carries a plurality of removable identification panels, each of which is removable for transferring and adhering to a third container, and each of the third panels carries a unique tracking identifier.

In another aspect a blood container label is provided comprising a first panel, including oppositely facing first and second surfaces, the first surface comprising an adhesive for attachment to a blood container. The label also includes a second panel removably carried on the second surface of the first panel. The second panel carries a plurality of removable identification panels, each including a first surface for attachment to a blood container and an oppositely facing surface carrying a unique donation identification number.

In a related aspect, a method is provided for tracking blood or blood components. The method includes substantially permanently adhering a first panel to an exterior surface of a whole blood container for collecting whole blood from a donor and removably adhering a second panel, smaller than the first panel, to an exterior surface of the first panel. The second panel carries a plurality of removable identification panels, each of which is removable for transferring and adhering to another container, and each of the identification panels carries a unique tracking identifier.

Blood Container/Processing Device and System

In one aspect, a single blood collection container is provided, comprising: a pair of facing flexible plastic sheets sealed together along a seal line to define an internal cavity for receiving blood, the cavity having a first end, a second end, a first side and a second side. An inlet port and outlet port extend through the seal line at the first end for flowing blood into and from the container, the seal line is uninterrupted except for the inlet and outlet ports. Inlet tubing is connected to the inlet port and extends to a distal or second end for connection to a vascular access member. Outlet tubing has a first end connected to the outlet port and a second end, sealed to preserve sterility, for sterile connection to a blood processing set by a sterile connection device on the blood processing apparatus. This single blood collection container may be used with any of the aspects summarized below, individually or in combination, and the aspects below may be independently employed with other containers, systems or methods.

In accordance with another aspect of the present subject matter, a blood collection container is provided that comprises a pair of facing flexible plastic sheets sealed together along a seal line to define an internal cavity for receiving blood, the cavity having a first end, a second end, a first side and a second side. An inlet port and outlet port extend through the seal line at the first or second ends for flowing blood into and from the container, and a hanging aperture is located on at least one of the first and second sides.

In another aspect, an integrated container system may be provided comprising a pair of facing flexible plastic sheets sealed together to define at least two separate internal cavities, one for receiving blood and another pre-filled with a selected amount of red cell additive fluid. Each cavity is defined by a separate seal line extending around the respective cavity, and each cavity includes a first end, a second end, a first side and a second side. The containers are integrally connected by a plastic web extending between sides of the cavities. A blood cavity inlet port and a blood cavity outlet port extend through the respective blood cavity seal line at the first end of the blood cavity for flowing blood into and from the container, and the seal line is uninterrupted except for the inlet and outlet ports. An additive fluid cavity access port and an additive fluid cavity outlet port extend through the additive fluid cavity seal line at the first end of the additive fluid cavity, and the seal line is uninterrupted except for the access and outlet ports.

In accordance with another aspect, a durable blood processing device is provided for cooperative association with a disposable blood or blood component processing circuit that includes a plurality of separate processing circuit modules for mounting cooperatively on the processing device, one of which modules includes a rotatable blood separator, and the processing device includes a receiving station for the rotatable blood separator and a drive system at the station for rotating the separator. At least two of the processing circuit modules each includes a thermoplastic fluid flow tubing segment, and the processing device includes a sterile connection device for receiving the tubing segments and automatically connecting the tubing segments to one another in a sterile manner for fluid flow therethrough upon user activation of the device.

These and other aspects of the present subject are set forth in the following detailed description of the accompanying drawings.

DESCRIPTION OF DRAWINGS

FIG. 1A is a perspective view of a blood processing system employing a reusable durable portion and a disposable fluid flow circuit formed from a plurality of fluid flow sub-systems or modules.

FIG. 1B is a perspective view of the blood processing system of FIG. 1, taken from a different angle.

FIG. 2 is a front view of a single whole blood collection container.

FIG. 3 is a front view of an integrated whole blood collection container and additive solution container.

FIG. 4 is a flow diagram depicting a blood or blood component container label system and its method of use.

FIG. 5 is a flow diagram depicting another blood or blood component container label system and its method of use.

FIG. 6 is a flow diagram depicting a further blood or blood component container label system and its method of use.

DESCRIPTION

Blood Processing System

Figure 7:
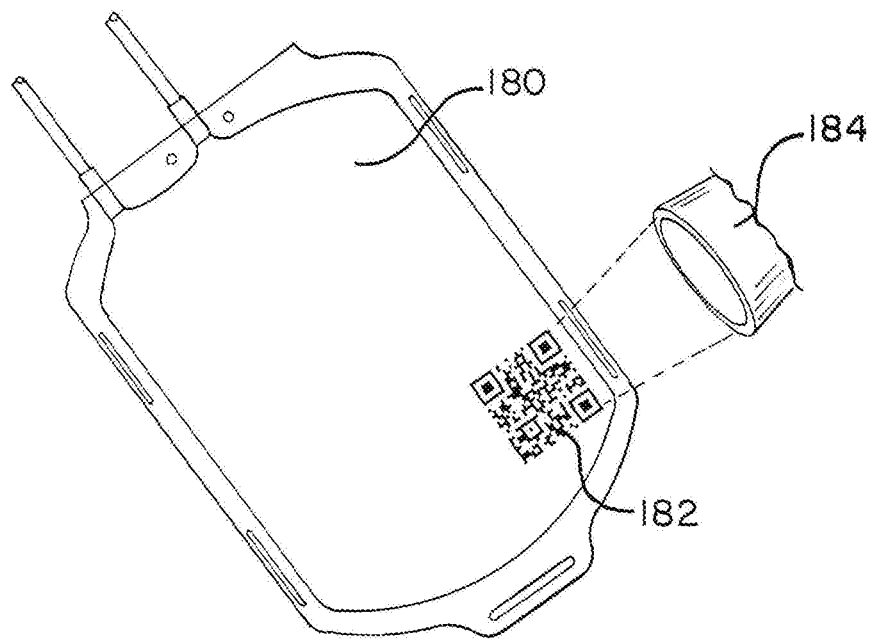
FIG. 7 is a perspective diagrammatic view of a blood or blood component container with a two dimensional barcode, and a scanner for scanning the barcode.

FIG. 1 depicts a blood processing system, and particularly a post-collection blood processing system, generally at 10, which includes a durable reusable processing device 12 and a disposable fluid flow circuit 14 for processing collected whole blood. The illustrated blood processing device 12 includes associated pumps, valves, sensors, displays and other apparatus for configuring and controlling flow of blood and additive solution through the disposable circuit. The device and the processing may be directed by an internal controller that includes a programmable microprocessor automatically controlling the operation of the pumps, valves, sensors, etc.

More specifically, the illustrated processing device includes user input and output touch screen 16, a pump station including a whole blood pump 18, an RBC pump 20 and an additive solution pump 22, blood separator mounting station and drive unit 24, leukocyte filter housing 26, tubing clamp/RF sealer/sensors 28a-d, sterile connection or docking devices 30a-b, tubing clamps 32a-b, hematocrit sensor 34 and container scanners 36. The processing device also includes hangers 38a-d, each associated with a weight scale, for suspending the various containers of the disposable fluid circuit.

As shown, the fluid flow circuit is provided in three separate modules, each of which is individually pre-assembled, and which are joined together on the processing device. These modules are—(i) an additive solution module that includes a pre-filled additive solution container 40 and associated fluid flow tubing 42 for withdrawing the additive solution, (ii) a whole blood module that includes at least the whole blood container 44 and associated fluid flow tubing 46 for withdrawal of collected whole blood from the container, and (iii) a processing module that includes pump cassette 48, membrane separator 50, red blood cell (RBC) container 52, plasma container 54, leukoreduction filter 56 (as shown, located within housing 26) and associated connecting tubing. The pump cassette 48 routes the fluid flow through three tubing loops that extend from the cassette, and each loop is uniquely positioned to engage a particular one of the pumps 18-22. The tubing may extend through the cassette or the cassette may have preformed fluid flow paths that direct the fluid flow. The membrane separator employs a membrane covered rotor within a stationary housing, as described earlier, for separating plasma from the cellular components of whole blood, and is rotated by a magnetic drive unit associated with the mounting station 24.

The modules are individually positioned on the processing device 12. With respect to the whole blood module, the whole blood container 44 is suspended on weight scale hanger 38a on the front of the processing device, and the associated fluid flow tubing 46 extends from the lower end of the whole blood container, through the hematocrit sensor 34, tubing clamp 32a and to the sterile connection device 30a where it will eventually be joined with tubing from the processing module.

With reference to the additive solution module, the additive solution container 40 is suspended on weight scale hanger 38b on the side of the processing device, and the associated fluid flow tubing 42 extends from the lower end of the additive solution container, through the additive fluid tubing clamp 32b and to the sterile connection device 30b, where it will be joined with tubing from the processing module.

Turning to the processing module, the membrane separator 50 is placed in association with the separator mounting/drive station 24. The pump cassette 48, through which fluid flow is routed for pump control, is mounted at the pumping station PS adjacent to the pumps 18-22, so that the tubing loops that extend from the cassette are positioned in registration with and preferably for automatic feeding onto one of the particular pumps 18-22. Whole blood tubing segment 58 extends from the cassette to the sterile connection device 30b for automatic connection to the tubing 46 associated with the whole blood container 44. The whole blood tubing segment or its flowpath continues through the cassette, forming an external tubing loop for cooperation with whole blood pump 18, which is illustrated as a rotary peristaltic pump, and then continues from the cassette to a whole blood inlet 60 of the membrane separator 50.

The membrane separation device separates the whole blood into plasma and red cell concentrate (which may include other cellular components such as platelets and white cells). The plasma is directed from the separator into the pre-attached plasma container 54, which is suspended on weight scale hanger 38c on the front of the processing device 12. For flowing plasma from the membrane separator 50 into the plasma container, tubing segment 62 connects the plasma container and a plasma outlet 64 of the membrane separator and extends through the clamp/sealer/sensor 28a.

Concentrated red cells (RBCs) flow from the membrane separator 50 through red cell exit port 66 of the membrane separator and through red cell fluid flow tubing segment 68, into the pump cassette 48. The red cell tubing segment 68 continues to the cassette and forms an external tubing loop for cooperation with red cell pump 20. From the cassette, the red cell tubing segment continues upwardly and over to the leukocyte reduction filter 56, which removes white blood cells from the red cell concentrate. From the leukocyte reduction filter, the RBC tubing segment extends through clamp/sealer/sensor 28b and into the red cell storage container 52, which is suspended from a weight scale hanger 38d on the side of the processing device.

To help preserve the viability of the red cells, the additive solution from the additive solution container 40 is added to the red cell container. Specifically, the additive solution flow tubing 42 is connected, by sterile connection device 30b, to an additive flow tubing segment 70 that is part of the processing module. The tubing segment 70 extends to the cassette 48, and additive solution flows through an external loop cooperating with additive solution pump 22. Downstream of pump 22, the additive solution flows into RBC flowpath (tubing segment 68 or a preformed flowpath) within the cassette, where it mixes with the RBC's. Thereafter the combined additive solution and RBC's flow through the RBC tubing segment 68 to filter 56 and into container 52.

Tubing segment 72 extends between the cassette 48 (where it communicates with the RBC flowpath) and the RBC storage container 52, generally parallel to the RBC tubing segment 68. This segment is filled with blood from the container and sealed at spaced apart locations by the blood processing personnel to provide a series of blood-filled "segments" that may be later severed for sampling, testing or cross-matching.

This tubing segment 72 also provides a pathway that allows removal of residual air from the RBC container after processing is completed. The pumps may be used to pump residual air from the RBC container to the empty whole blood container through tubing segment 72 and eventually back to the whole blood container 44.

Tubing segment 72 has one additional benefit. It may be used to flow RBC's directly into the RBC container 52 and bypassing the filter 56. This is particularly useful in situations where RBC cannot be filtered, such as known physiological reasons, for example in donors suffering from sickle-cell anemia. For those, the filter can be bypassed and plasma can still be processed and collected.

As explained above, the disposable fluid circuit 14 is assembled from separate modules in the illustrated embodiment and sterile connection (sometimes called sterile docking) devices 30a-b are provided for connecting fluid flow tubing of the different modules. The sterile connection devices may employ any of several different operating principles. For example, known sterile connection devices and systems include radiant energy systems that melt facing membranes of fluid flow conduits, as in U.S. Pat. No. 4,157,723, heated wafer systems that employ wafers for cutting and heat bonding or splicing tubing segments together while the ends remain molten or semi-molten, such as in U.S. Pat. Nos. 4,753,697, 5,158,630 and 5,156,701, and systems employing removable closure films or webs sealed to the ends of tubing segments as described for example in U.S. Patent Application Publication No. 2014/0077488. All of the above are incorporated by reference in their entirety.

More recently, systems have been disclosed for forming sterile connections employing a different technique, wherein a sealed tubing segment is compressed or pinched, heated and the sealed end severed. The tubing is then joined to a similarly treated tubing segment. A detailed description of this type of device may be found in U.S. Patent Application Publication No. 2013/0153048 and U.S. patent application Ser. No. 14/309,305, filed Jun. 19, 2014, both of which are hereby incorporated by reference in their entirety. This is the type of sterile connection device particularly contemplated for use as sterile connection devices 30a-b in the blood processing device 12 as described above, although sterile connection devices based on other operating principles may also be employed.

Further, as shown in FIGS. 1A and 1B, the illustrated processing device 12 includes a scanner 36 associated with and facing each of the containers. Each scanner is configured to view or read a barcode and/or other information on the facing side of the particular container (such as on a label) and to communicate information contained or encoded in the barcode, an image of all or a portion of a label, and/or other information to the device processor and/or to a local or remote data management system for recording as part of a process record, tracking and/or quality control purposes. The information may be communicated in any suitable manner, and the device may be configured to communicate the information via direct wire connection, internet, LAN, WIFI, Bluetooth or other suitable communication means. As described below, the imager may also read or image other information on the container or on a container label.

Blood Containers

Turning now to a different and independent aspect of the present subject matter, FIG. 2 depicts a single whole blood collection container and tubing set or module. The container 80 is formed from a pair of facing flexible plastic films or sheets 82, which may be made of any suitable heat-sealable material such as, but not limited to, polyvinylchloride. The container has an internal cavity with a first end 84, opposed second end 86, first side 88 and opposed second side 90. The sheets are sealed together, as by radio frequency (RF) or heat seal, along a seal line 92 that extends around the entire periphery of the container and is uninterrupted except for inlet port 94 and outlet port 96 located at the first end of the container cavity. The position of the ports may vary, but in the illustrated embodiment, the inlet port 94 is between the outlet port and the second side 90 of the container, and preferably substantially adjacent to the corner or junction between the first end and second side. The outlet port 96 is illustrated as being generally midway between the first and second sides. Alternatively, it should be noted that ports 94 and 96 may be either inlet or outlet ports, depending on intended usage.

Inlet port 94 is connected to inlet flow tubing 98, which extends to a pre-attached venous access device 100, such as a needle, or to connector, such as a standard luer lock, for connection to a needle. The inlet flow tubing 98 may have additional ports or connection sites as desired, such as for pre-donation sampling or the like. It may also include an internal frangible valve 102 that normally blocks flow through the tubing and can be opened by manual manipulation or bending of the tubing, such as disclosed for example in U.S. Pat. Nos. 4,386,622, 4,181,140, and 4,270,534, all of which are incorporated by reference.

Outlet fluid flow tubing 104 extends from the outlet port 96 to a sealed distal end 106. The tubing 104 has a length sufficient to extend from the container 80 to a sterile connection device, such as the sterile connection device 30b located on processing device 12. While the length may vary depending on the configuration of device 12, to extend through the illustrated hematocrit sensor 34 and clamp 32a and to the sterile connection device 30a, a length of about 10-20 inches (25.4-50.8 cm), e.g., 13-14 (such as 13.5) or 17 inches (33.0-35.6 (such as 34.3) or 43.18 cm), may be used for an arrangement such as shown in the figures. Use of outlet tubing separate from the inlet tubing helps prevent introduction of blood clots into a downstream processing module or system if the user fails, at the time of collection, to express any blood remaining in the inlet tubing (also called stripping the blood) into the container.

Hanging apertures, shown for purposes of illustration and not limitation as slits 108, are provided in the seal line 92 to allow for suspending the container, such as from weight scale hook as employed in the processing device 12. The slit 108 located in the second end 86 of the container 80 allows the container to be suspended vertically and the slits along the sides of the container allow it to be suspended so that it hangs in a direction other than vertically, such as horizontally or at an downward angle such as shown in FIG. 2, where the inlet port 94 is slightly lower than the outlet port 96 by distance D. Hanging in this position allows any solids in the collected blood, such as clots, to settle away from the outlet port, and helps avoid blocking of the outlet flow tubing 104 by such solids or introduction of such solids into downstream processing system components.

The number of slits 108 and location may vary. While, in FIG. 2, two slits are shown on each side of the container with a single end slit, a single slit could also be used on one or both sides, and such slit could be centered or located off-center. The end slit could be eliminated to allow only non-vertical hanging. Or, the side slits could be omitted and only a single end slit used for a container limited to vertical hanging. Providing multiple slits as shown in FIG. 2 allows the user to choose the desired hanging position.

FIG. 3 shows an integrated container system 110 having two discrete container cavities—an additive solution cavity within container 112 and a whole blood collection cavity within container 114. The cavities or containers are integrally joined by intermediate web 116.

The integral containers are formed of two facing flexible plastic sheets or films, sealed together such as by RF or heat sealing. Each container is defined by a separate seal line and is generally rectangular in configuration with opposed ends and sides. The additive solution container or cavity 112 is formed by seal line 118 that extends along first end 120, first side 122, second end 126 and second side 128. The seal line is uninterrupted except for outlet port 130 and access port 132 in the first end of the container. The access port allows for the addition of additive fluid into the container 112 during manufacture, and outlet port 130 is attached to a length of fluid flow tubing 134 sealed at the distal end for connection, preferably sterile connection, to a processing set or module.

The whole blood container or cavity 114 is formed by seal line 136 that extends along first end 138, first side 140, second end 142 and second side 144. The seal line is uninterrupted except for outlet port 146 and inlet port 148 in the first end of the container. The inlet port allows the inflow of whole blood during collection, and the outlet port directs fluid flow to a downstream processing set or module. The inlet port also allows the addition of anticoagulant solution into the container during manufacturing. Inlet flow tubing 150 extends from the inlet port, and outlet tubing 152 extends from the outlet port. The inlet and outlet tubing 150 and 152 may be configured similarly to the inlet flow tubing 98 and outlet flow tubing 104 described earlier with respect to the container in FIG. 2.

The first side 122 of the additive solution container 112 is attached to the second side 144 of the blood container 114 by the integral intermediate web 116 that is part of the original plastic sheets used in forming the containers and extends between the containers. This web may be of such width as desired and allows the containers to be folded into a more compact arrangement if desired for shipping or handling.

Labeling/Tracking

FIGS. 4-6 are directed to another independent aspect of the present subject matter—a system and method for identifying and tracking blood and blood components. FIG. 4 is a flow chart that illustrates apparatus and steps employed in one embodiment. At the top of FIG. 4 is shown is an exemplary blood container 160 in the form of a bag or pouch, and may be for example the single container of FIG. 2. A first panel or sticker 162 is substantially permanently pre-attached to an outer surface of the container. A second panel or sticker 164, which may be smaller than the first panel, is releasably pre-attached to the outer surface of the first panel. The first panel has an outer edge or first panel perimeter (defined by its side and end edges, 1S and 1E respectively) and the second panel may be smaller so as to fit entirely within the first panel perimeter. The surface of the first panel that is beneath the second panel may comprise a release surface that allows removal of the adhesive-backed second panel, or the second panel may employ a releasable adhesive for releasable attachment to the first panel.

As shown in the second step of FIG. 4, at or before the time of actual collection of blood in container 160, a third panel or sticker 166 is permanently attached onto the second panel, such as by the technician or phlebotomist. The third panel includes a plurality of removable uniquely coded donation identification number (DIN) identification panels, such as stickers, 168 that can be used to identify a particular donation and trace the source of blood components from the donation. The second panel has an outer edge or perimeter, defined by its side and end edges, 2S and 2E respectively, and the third panel may be smaller than the second panel and sized to fit entirely within the second panel perimeter. Similarly, the identification panels may be sized to fit entirely within the perimeter of the third panel (also defined by side and end edges of the third panel, 3S and 3E respectively). In the next illustrated step, during post-collection processing, when the red cells are concentrated and transferred into another container 170, the second panel 164 (with the third panel and DIN panels, such as stickers, attached) is removed from the whole blood container and placed and adhered onto the concentrated red cell container 170. For later blood type verification or other testing, samples of red cells may be removed from red cell container into a sample container such as a tube or vial 172, as illustrated in the final step of FIG. 4. At that time one of the DIN identification panels, e.g., stickers, can be removed from the panel on the red cell container and may be permanently adhered to the sample container so that traceability of the blood sample is maintained. The second panel may comprise a release surface that allows removal of the adhesive-backed DIN identification panels, or the DIN panels may employ an adhesive that is releasable from the third panel.

An alternative arrangement and sequence is illustrated in FIG. 5. In that alternative the whole blood container 160 does not have the first and second panels 162 and 164 pre-attached to the container. Instead, the first and second panels are separately pre-attached for convenience, and the first panel is permanently adhered to the surface of the blood container before or at the time of blood collection. At that time, the third panel 166 with DIN identification panels, e.g., stickers, 168 thereon is permanently attached to the second panel as described above, allowing the remaining steps discussed above to be carried out and traceability maintained.

A further alternative is shown in FIG. 6, which is similar to FIG. 5, except that the second panel itself is subdivided into a plurality of DIN identification panels or stickers that are pre-printed and can be removed or peeled off (e.g., from a release layer or by use of a releasable adhesive) for attachment to a sample tubing or vial. This eliminates the need for a separate third panel of DIN stickers that is permanently attached to the second panel.

Blood Container with Two Dimensional Barcode/Authentication

Turning now to another independent aspect of the present subject matter, FIG. 7 illustrates a particularly efficient arrangement for information transfer and recordation. Shown there is an example of a blood or blood component container 180 of the general type, such as the single container of FIG. 2, discussed above. A two dimensional barcode 182 is located on the container, and may contain important information useful in tracking and quality control, and can be scanned by a scanner 184. Currently, the pertinent regulatory authorities allow information to be placed at particular locations on the container. For some types of information, the information is required to be spaced sufficiently far apart or on different sides of the container and cannot be read or scanned by a single imager or scanner in a fixed location on the processing instrument. An example of this is the manufacturer's part number or catalogue number, which may be on the back of the container, and the product expiration date, which may be on the bottom right corner of the front of container.

A two dimensional barcode has the capability of storing a large amount of information, much more than the typical single dimension or linear barcode. In accordance with the present aspect, a two dimensional barcode is employed that contains pertinent manufacturer's data in a location on a container or container label that is preferably facing or otherwise visible from a fixed scanner 184 on the processing device, similar to scanners 36 shown in FIGS. 1A and 1B. A "two dimensional barcode" is not limited to a particular code format, specification or standard, but it is intended to be a general term, used in accordance with its ordinary meaning, which refers to a two dimensional representation or matrix, that contains or encodes information based on dark and light spots or areas within the matrix, which matrix is typically but not exclusively square or rectangular, and in contrast to a one-dimensional barcode based on a series of lines and spaces. The stored or encoded information may include, without limitation, any one of the manufacturer's part number or catalogue number for the container or module, lot number, expiration date, product code for the blood product to be contained in it and other such information, alone or in any desired combination. A part number or catalogue number may be particularly beneficial to encode, either alone or in combination with a product expiration date. Optionally, the barcode may include any additional manufacturer information required by the United States Consensus Standard for the Uniform Labeling of Blood and Blood Components. This does not preclude the required information from also appearing elsewhere to meet regulatory requirements, but having this information encoded into a single two dimensional barcode allows a single scanning device to read/image all the information automatically and without user manipulation, so that the information can be retained as part of the stored process record.

Figure 8:
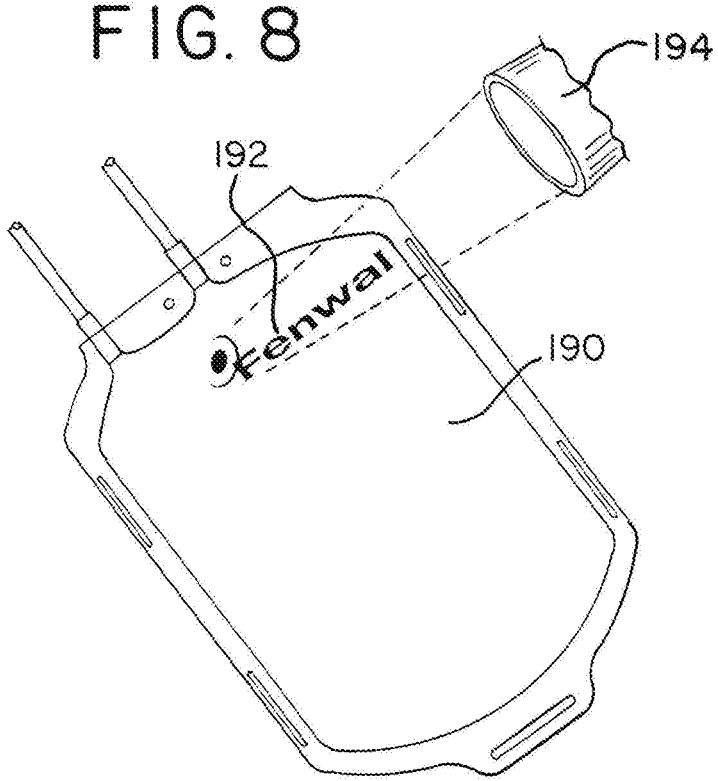
FIG. 8 is a perspective diagrammatic view of a blood or blood component container with a trade logo, and a scanner for scanning the trade logo.

In another independent aspect of the present application, FIG. 8 diagrammatically depicts a blood container 190 bearing a trade logo or identifier 192 of unique design or configuration associated with a particular source that can be scanned by a scanner 194 to determine and authenticate that the disposable is genuine and is what it purports to be—in this case a product of that particular source—in this case, Fenwal Inc. "Trade logo" as used herein is intended to be general and may include any design and/or combination of numbers or letters or designs that is identified with a particular source of the product. Trade logo may include a registered trademark, but is not limited to such.

More specifically the processing device employing such a system could include a programmable control processor and onboard data storage, lookup table or the like (or access to remote data storage) of selected characteristics of such a trade logo on a genuine container, e.g., a genuine Fenwal blood component container. Such characteristics could be any one or more of numerous aspects, including without limitation one or more characteristics such as the position coordinates of the logo on the container, spacing between certain numbers or letters contained in the logo, font or image size, ratios of sizes of certain aspects such as ratios of different font sizes, density of the image or ink density on certain parts of the logo, logo image resolution and logo ink material. The detected characteristics of the container in question would be compared to the stored reference characteristics of the logo on a genuine product and, based on the comparison, the controller would determine if the detected and stored characteristics are the same or sufficiently the same for the product in question to be deemed genuine. If not, the controller could generate an alarm or alert condition, such as an audio, visual or other signal, or even disable operation of the processing device until an operator intervenes.

The scanner 194 for this application could be a separate from the barcode scanner described above or, if practicable, combined into a single scanner or scan unit, such as scanner 36 on the processing device of FIGS. 1A-B. As with the two dimensional barcode discussed above, the trade logo 192 is preferably on a surface of the container or a container label facing the processing device when the container is suspended thereon, so that the logo can be scanned automatically without the need for user manipulation.

Figure 9:
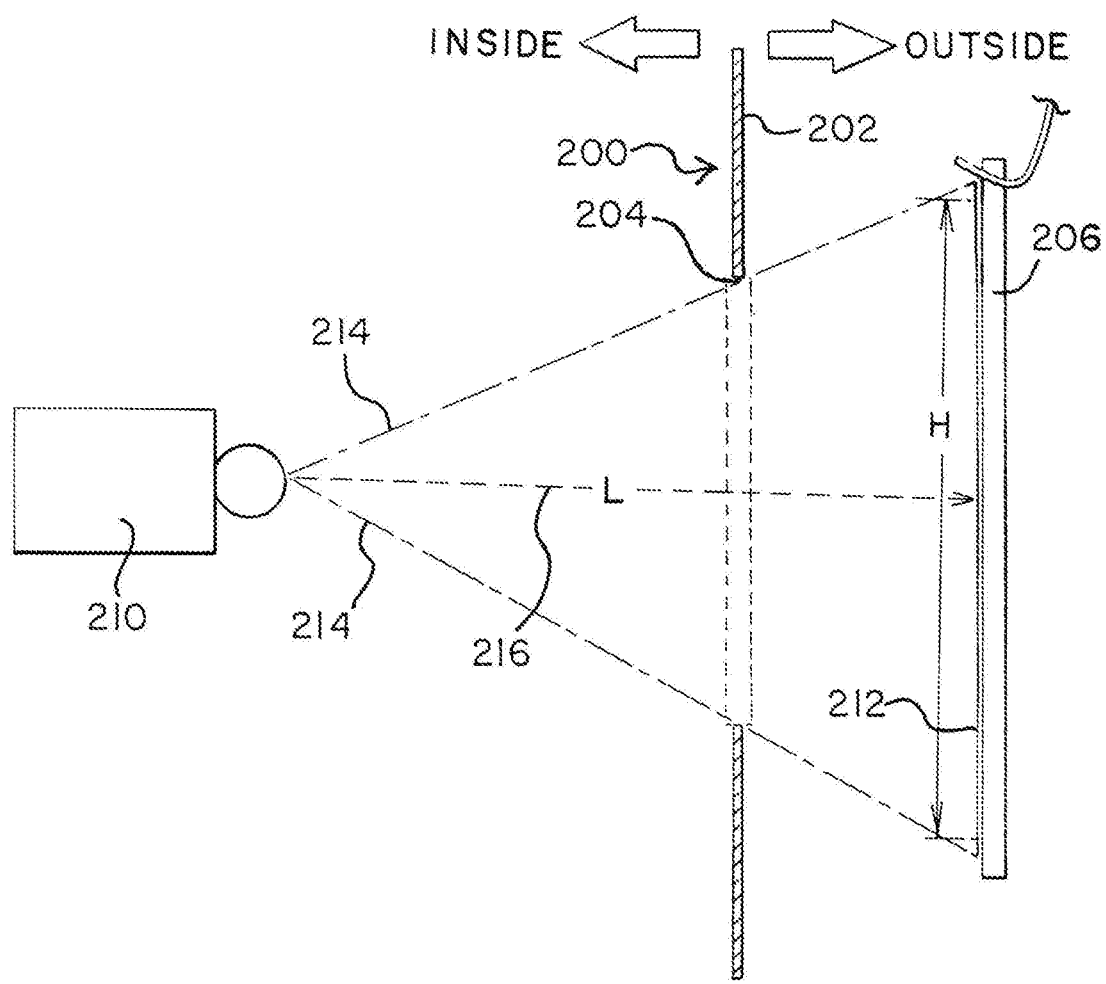
FIG. 9 is a diagrammatic cross-section of a medical fluid processing device, such as the blood processing device of FIGS. 1A and 1B, showing positioning of a scanner in the processing device.

FIG. 9 diagrammatically shows the positioning of a scanner/imager in a medical fluid processing device, such as the blood processing device 12 of FIGS. 1A-B. As shown in partial view there, the processing device has a housing 200 with a wall 202 and an aperture in the wall forming a window 204. The window is located adjacent to where a container 206, such as a blood or blood component container, additive solution container or other container, would hang when suspended from a hanger 208 or other suspension member (e.g., a clamp) on the processing device. The window 204 preferably employs glass that is shielded against electromagnetic interference. Scanner 210 is located within the housing 200, behind window 204. Similar configurations may be seen in FIGS. 1A-B, where a scanner 36 is located on the processing device behind and facing each container 40, 44, 52 and 54.

Scanner 210 may be of any suitable design or employ any suitable technology for scanning, imaging or otherwise capturing two dimensional barcodes, logos and/or blood container labels, as described herein. For example, the scanner 210 may employ a laser, camera, CCD scanner, or other suitable imaging or scanning device or technology. One non-exclusive example of an imager/scanner that may be employed here is the model JE-227 scan engine or similar device from Jadak Technologies, Inc., with offices in North Syracuse, N.Y.

As noted above, the scanner 210 is preferably mounted within the housing 200 for protection and positioned to optically view or scan the container 206 through the window 204. The scanner is positioned so that it scans or images a particular surface area of the container. More specifically, in connection the present subject matter the scanner is preferably positioned to image a label 212 on the surface of the container facing the window, which label has information to be recorded as part of a process record. The information could be in the form of or encoded in a barcode (e.g., the two dimensional barcode discussed earlier) and/or a trade logo. In the medical field in general and in the field of blood collection and processing in particular, aspects of the container and container label may be subject to certain requirements of regulatory or standard-setting bodies. Typically, labels on containers for blood or blood components are rectangular and have a size of about 4 inches (102 mm) in width and 4 inches (102 mm) in length. ISO3826 standard shows a label for a blood component container having a label size of 105 mm×105 mm (4.1 inches×4.1 inches). The labels may also need to comply with other standards such as ISBT-128, ST-005 which requires the container to carry a Base Label of 100+/−2 mm×106+/−2 mm (3.9 inches×4.2 inches). Thus, these labels are generally within a space of 4+/−0.25 inches×4+/−0.25 inches. For purposes of this description the above labels, even though slightly larger or smaller, are deemed to be substantially 4 inches×4 inches.

Advantageously the scanner 210 in the illustrated embodiment is configured to image the entire or substantially the entire label 212 including, if present on the label, a barcode, such-as a two dimensional barcode, for product information recordation and a trade logo for authentication purposes. To achieve this, the scanner is particularly positioned within the housing. In the illustrated embodiment, the scanner 210 has a field of view 214 (which can have vertical and horizontal aspects—only vertical being shown in FIG. 9) and focal length or distance 216. To image the desired surface area of a blood or blood component label having a label area of about 4 in×4 in, a scanner having a vertical field of view of about 30-40 degrees and an equal or larger horizontal field of view, could be positioned about 6-8 inches (about 15-20 cm) from the surface of a suspended container. This configuration may vary based on the size of the particular area to be imaged and the particular scanner employed, without departing from the present disclosure. As noted earlier, one non-exclusive example of a scanner that may be employed in this subject matter is the model JE-227 scan engine or a similar device available from Jadak Technologies, Inc., with offices in North Syracuse, N.Y.

While the various independent and related aspects of the present subject matter have been described by reference to specifically illustrated structures and methods shown in the accompanying figures, it is understood that the present subject matter is not limited to such specific structures or methods and has application in other forms and devices without departing from the scope of this disclosure. For this reason, reference is required to the following claims to ascertain the scope of the present subject matter.

The invention claimed is:

1. A blood processing device comprising:
   a housing having a first surface and a second surface, wherein the first surface is defined in a generally vertical plane and the second surface is defined in a different plane;
   a scanning system incorporated into the housing and including a window defined in the first surface of the housing and a scanner located within the housing, wherein the scanner is configured to scan a two-dimensional barcode through the window;
   a touch screen incorporated into the second surface of the housing;
   a container suspension device configured to suspend a blood container on the blood processing device;
   a tubing clamp associated with the housing and configured to accommodate a tube connected to a suspended blood container; and
   a controller located within the housing, wherein
      the controller is operatively coupled to the scanner, the touch screen, and the tubing clamp, and
      the controller is programmed to execute a procedure in which blood is conveyed through the tube.

2. The blood processing device of claim 1, wherein the scanning system is configured for scanning a selected surface area of a blood container through the window.

3. The blood processing device of claim 2, wherein the selected surface area is substantially the size of a label located on the blood container.

4. The blood processing device of claim 2, wherein the selected surface area comprises a generally rectangular area of substantially 4 inches in length and 4 inches in width.

5. The blood processing device of claim 1, wherein the scanning system is configured for scanning a selected surface area of a suspended blood container through the window.

6. The blood processing device of claim 5, wherein the scanner is located so as to be about 6-8 inches from the surface of a suspended blood container to be scanned.

7. The blood processing device of claim 5, wherein the scanner has a field of view and is located within the housing so as to be at a selected focal length from the surface of a suspended blood container to be scanned so that the field of view substantially includes the entire selected surface area.

8. The blood processing device of claim 1, wherein the window comprises glass shielded against electromagnetic interference.

9. The blood processing device of claim 1, wherein the controller is programmed to store and/or communicate information scanned from the two-dimensional barcode.

10. The blood processing device of claim 1, further comprising a weight scale associated with the container suspension device and operatively coupled to the controller.

11. A system comprising a disposable blood processing circuit and a durable blood processing device cooperatively associated with the blood processing circuit for controlling flow through the blood processing circuit, wherein
the blood processing circuit includes a blood container and a tube connected to the blood container; and
the blood processing device includes
a housing having a first surface and a second surface, wherein the first surface is defined in a generally vertical plane and the second surface is defined in a different plane,
a scanning system incorporated into the housing and including a window defined in the first surface of the housing and a scanner located within the housing, wherein the scanner is configured to scan a two-dimensional barcode through the window,
a touch screen incorporated into the second surface of the housing,
a container suspension device configured to suspend the blood container on the blood processing device,
a tubing clamp associated with the housing and configured to accommodate the tube connected to a suspended blood container, and
a controller located within the housing, wherein
the controller is operatively coupled to the scanner, the touch screen, and the tubing clamp, and
the controller is programmed to execute a procedure in which blood is conveyed through the tube.

12. The system of claim 11, wherein the scanning system is configured for scanning a selected surface area of a blood container through the window.

13. The system of claim 12, wherein the selected surface area is substantially the size of a label located on the blood container.

14. The system of claim 12, wherein the selected surface area comprises a generally rectangular area of substantially 4 inches in length and 4 inches in width.

15. The system of claim 11, wherein the scanning system is configured for scanning a selected surface area of a suspended blood container through the window.

16. The system of claim 15, wherein the scanner is located so as to be about 6-8 inches from the surface of a suspended blood container to be scanned.

17. The system of claim 15, wherein the scanner has a field of view and is located within the housing so as to be at a selected focal length from the surface of a suspended blood container to be scanned so that the field of view substantially includes the entire selected surface area.

18. The system of claim 11, wherein the window comprises glass shielded against electromagnetic interference.

19. The system of claim 11, wherein the controller is programmed to store and/or communicate information scanned from the two-dimensional barcode.

20. The system of claim 11, further comprising a weight scale associated with the container suspension device and operatively coupled to the controller.

* * * * *